United States Patent
Nasir et al.

(10) Patent No.: US 6,482,601 B1
(45) Date of Patent: Nov. 19, 2002

(54) FLUORESCENCE POLARIZATION-BASED HOMOGENEOUS ASSAY FOR FUMONISIN DETERMINATION IN GRAINS

(75) Inventors: Mohammad Sarwar Nasir, Grayslake, IL (US); Michael E. Jolley, Round Lake, IL (US)

(73) Assignee: Diachemix LLC, Milwaukee, WI (US)

(*) Notice: Subject to any disclaimer, the term of this patent is extended or adjusted under 35 U.S.C. 154(b) by 0 days.

(21) Appl. No.: 09/659,663

(22) Filed: Sep. 11, 2000

(51) Int. Cl.[7] .................... G01N 33/569; G01N 33/536; C07K 16/14
(52) U.S. Cl. ....................... 435/7.31; 435/341; 435/810; 435/975; 436/536; 436/537; 436/17; 436/172; 436/177; 436/825; 530/371; 530/388.5; 530/389.1; 530/823
(58) Field of Search .......................... 435/7.31, 70.21, 435/341, 975, 810; 436/518, 536, 537, 17, 172, 177, 800, 825, 826; 530/371, 388.5, 389.1, 806, 823

(56) References Cited

U.S. PATENT DOCUMENTS

| | | | | |
|---|---|---|---|---|
| 4,420,568 A | * | 12/1983 | Wang et al. | 436/536 |
| 4,476,229 A | * | 10/1984 | Fino et al. | 436/537 |
| 5,427,960 A | * | 6/1995 | Wang et al. | 436/536 |
| 5,976,820 A | * | 11/1999 | Jolley et al. | 436/536 |
| 6,110,750 A | | 8/2000 | Sugden et al. | 436/537 |

FOREIGN PATENT DOCUMENTS

| | | |
|---|---|---|
| WO | 0017649 | 3/2000 |
| WO | 0019202 | 4/2000 |

OTHER PUBLICATIONS

Thompson et al., 1996. Fiber–optic immunosensor for the detection of fumojinsin B1. J. Agric. Food Chem. 44: 1041–1046, 1996.*
Kulisek et al., 2000. Comparison of extraction buffers for the detection of fumonisin B1 in corn by immunossay and high–performance liquid chromatography. J. Agric. Food Chem. 48: 65–69, Dec. 1999,*
Azcona–Olivera et al., Production of monclonal antibodies to the mycotoxins fumonisins B1, B2, and B3. J. Agric. Food Chem. 40: 531–534, 1992.*
Fukuda et al., 1994. Preparation and characterization of anti–fumonisin monoclonal antibodies. Biosci. Biotech. Biochem., 58: 765–767, 1994.*
Maragos, et al., "Fiber–optic Immunosensor for Mycotoxins," *Natural Toxins*, 7:371–376 (1999).
Scott, P. M. "Fumonisins" *Int. J. Food. Microbiol.* 1993, 18, 257–270.
Shephard, G. S.; Sydenham, E. W.; Thiel, P. G.; Gelderblom, W. C. A. "Quantitative determination of fumonisins $B_1$ and $B_2$ by HPLC with fluorescence detection." *J. Liq. Chromatogr.* 1990, 13, 2077–2087.

Sydenham, E. W.; Gelderblom, W. C. A.; Thiel, P. G.; Marasas, W. F. O. "Evidence for the natural occurence of fumonisin $B_1$, a mycotoxin produced by Fusarium moniliforme, in corn." *J. Agric. Food. Chem.* 1990, 38, 285–290.
Thiel, P. G.; Sydenham, E. W.; Shephard, G. S.; Vanschalkwyk, D. J. "Study of the reproducibility characteristics of a liquid chromatographic method for the determination of fumonisin B–1 and B–2 in corn." *J. AOAC Int.* 1993, 76, 361–366.
Bennettt, G. A.; Richard, J. L. "Liquid chromatographic method for analysis of the Naphthalene Dicarboxaldehyde derivative of fumonisins." *J. AOAC Int.* 1994, 77, 501–506.
Sydenham, E. W.; Shephard, G. S.; Thiel, P. G. "Liquid chromatographic determination of fumonisins $B_1$, $B_2$ and $B_3$ in foods and feeds." *J. AOAC Int.* 1992, 75, 313–318.
Wilson, T. M.; Ross, P. F.; Rice, L. G.; Osweiler, G. D.; Nelson, H. A.; Owens, D. L.; Plattner, R. D.; Reggiardo, C.; Noon, T. H.; Pickrell J. W. "Fumonisin B1 levels associated with an epizootic of equine leukoencephalomalacia." *J. Vet. Diagn. Invest.* 1990, 2, 213–216.
Bagneris, R. W.; Carter, L. Jr.; Guerrero, H. G.; Ware, G. M. "Rapid HPLC detection and survey of fumonisin B1 in corn and corn screenings using fluorescence detection." $106^{th}$ AOAC Int. Ann. Mtg., Cincinnati. 1992, 235.
Hansen, T. J.; Zabe, N. A.; Skipper, P. L. "Immunoaffinity isolation of fumonisin B1 and application to analysis in corn." $106^{th}$ AOAC Int. Ann.Mtg., Cincinnati. 1992, 230.
Norred, W. P.; Voss, K. A. "Toxicity and role of fumonisins in animal diseases and human esophageal cancer." *J. Food Prot.* 1994, 57, 522–527.
Rottinghaus, G. E.; Coatney, C. E.; Minor, H. C. "A rapid sensitive thin layer chromatography procedure for the detection of fumonisin B1 and B2," *J. Vet. Diagn. Invest.* 1992, 4, 326–329.
Usleber, E.; Straka, M.; Terplan, G. "Enzyme immunoassay for fumonisin B1 applied to corn based food." *J. Agric. Food Chem.* 1994, 42, 1392–1396.
Lynch, B. A.; Loiacono, K. A.; Tiong, C. L.; Adams, A. E.; MacNeil, I. A. "A fluorescence polarization based Src–SH2 binding assay." *Anal. Biochem.* 1997, 247, 77–82.

(List continued on next page.)

Primary Examiner—Christopher L. Chin
Assistant Examiner—James L. Grun
(74) Attorney, Agent, or Firm—McDonnell Boehnen Hulbert & Berghoff

(57) ABSTRACT

A homogeneous assay for determining the fumonisin content in grains uses the technique of fluorescence polarization. A grain extract is prepared by shaking a crushed grain sample with a solvent. A mixture is prepared by combining the grain extract with a tracer and with monoclonal antibodies specific to fumonisin. The tracer is able to bind to the monoclonal antibodies to produce a detectable change in fluorescence polarization. The tracer is prepared by conjugating fumonisin to a suitable fluorophore. The fluorescence polarization of the mixture is measured. The fumonisin concentration of the mixture may be calculated using a standard curve obtained by measuring the fluorescence polarization of a series of fumonisin solutions of known concentration.

16 Claims, 2 Drawing Sheets

OTHER PUBLICATIONS

Wei, A. P.; Herron. J. N. *Anal. Chem.* 1993, 65, 3372–3377.

Kauvar, L. M.; Higgins,D. L.; Viller, H. O.; Sportsman, J. R.; Engquist–Goldstein, A.; Bukar, R.; Bauer, K. E.; Dilley, H.; Rocke, D. M. *Chem. Biol.* 1995, 2, 107–118.

Jolley, M. E. "Fluorescence polarization immunoassay for the determination of therapeutic drug levels in human plasma," *J. Anal. Toxicol.* 1981, 5, 236–240.

Eremin, S. A.; Gallacher, G.; Lotey, H.; Smith, D. S.; Landon, *J. Clin. Chem.* 1987, 33, 4113–4122.

Jolley, M. E. "Fluorescence polarization assays for the detection of proteases and their inhibitors." *J. Biomol. Screen.* 1996, 1, 33–38.

Nielsen, K.; Gall, D.; Jolley, M.; Leishman, G.; Balsevicius, S.; Smith, P.; Nicoletti, P.; Thomas, F. *J. Immun. Methods*, 1996, 195, 161–168.

Nasir, M. S.; Jolley, M. E. Fluorescence Polarization: An analytical tool for Immunoassay and Drug Discov *Combinatorial Chemistry & High Throughput Screening*, 1999, 2, 177–190.

Tencza, S. B.; Islam, K. R.; Kalia, V.; Nasir, M. S.; Jolley, M. E.; Montelaro, R. C. "Development Fluorescence polarization–Based Diagnostic Assay for Equine Infectious Anemia Virus." *J. Clin. Microbiol.* 38, 1854–1859.

Azcona–Olivera, et al., *Applied and Environmental Microbiology*, Jan. 1992, 58(1):169–173.

Elissalde, et al., *Food & Agricultural Immunology*, 1995, 7:109–122.

Gelderblom, et al., *Appl. Environ. Microbiol.*, Jul. 1988, 54(7):1806–1811.

Maragos, et al., *Food and Agricultural Immunology*, 1997, 9:3–12.

Maragos, et al., *Food and Agricultural Immunology*, 1997, 9:147–157.

Maragos et al., *Food Additives and Contaminants*, 1996, 13(1):105–113.

Pestika, et al., *Food Technology*, Feb. 1995, pp. 120–128.

Sydenham et al., *Journal of Agricultural and Food Chemistry*, 1996, 44:159–164.

* cited by examiner

FLUORESCENCE POLARIZATION-BASED HOMOGENEOUS ASSAY FOR FUMONISIN DETERMINATION IN GRAINS

BACKGROUND OF THE INVENTION

1. Field of the Invention

This invention relates to the field of Mycotoxin assays. More particularly, this invention relates to a homogeneous assay that uses changes in fluorescence polarization to detect the presence of fumonisin in grains.

2. Description of Related Art

Fumonisins are mycotoxins produced mainly by *Fusarium moniliforme,* a common fungus found mostly in corns and corn products. Several different fumonisins have been identified, including fumonisin B1, B2, B3, and B4, and these are all characterized by a 20-carbon backbone, two tricarballylic acid groups, one to three hydroxyl groups, and a single primary amine. Fumonisin B1 is believed to be the most abundant form.

Fumonisin is the cause of leukoencephalomalacia (which is also referred to as LEM or spongy brain syndrome) in horses, cancer in laboratory animals, and esophageal cancer in humans.[1] Fumonisin levels greater than 10 parts per million (PPM) cause craziness in horses within a week, and levels greater than about 70 PPM can cause various liver diseases in pigs within four weeks. Due to the possible risk to human and animal health, extended research is underway to develop effective procedures for the determination of fumonisins.[8]

Being new, this toxin lacks a simple commercially available test kit for its quantitative analysis. Mass spectroscopy,[1b] TLC,[9] HPLC,[2-4] and ELISA (enzyme-linked immunosorbent assay)[7] are the known methods for fumonisin analysis. However, most of these assays require extended cleanup steps and derivatization after extraction in order to get rid of interfering substances. This becomes very time consuming and in turn hampers the fast analysis of fumonisins.

ELISA methods are relatively faster. However, they are hard to quantify and have limitations due to dilution and washing steps. ELISA methods are also undesirably labor intensive, in that they typically involve several washings, liquid transfers, and incubation times. Nevertheless, specific antibodies against fumonisin have been prepared by various groups.[10-11] Due to various limitations of different methods; a faster and simpler method for the determination of fumonisins is needed.

SUMMARY OF THE INVENTION

In a first principal aspect, the present invention provides a homogeneous assay for characterizing the fumonisin content in grains. In accordance with the method, fumonisin is extracted from a grain sample to provide an extract. The extract is then combined with a tracer and an antibody to provide a mixture. The antibody is specific for fumonisin. The tracer comprises fumonisin conjugated to a fluorophore, and the tracer is able to bind to the antibody to produce a detectable change in fluorescence polarization. The fluorescence polarization of the mixture is measured to obtain a measured fluorescence polarization. The measured fluorescence polarization is compared with a characterized fluorescence polarization value that corresponds to a known fumonisin concentration.

In a second principal aspect, the present invention provides an assay kit for characterizing fumonisin content in grains. The assay kit comprises an antibody and a tracer, each in an amount suitable for at least one assay, and suitable packaging. The antibody is specific for fumonisin. The tracer comprises fumonisin conjugated to a fluorophore, and the tracer is able to bind to the antibody to produce a detectable change in fluorescence polarization.

DETAILED DESCRIPTION OF THE PREFERRED EMBODIMENTS

Figure 1:
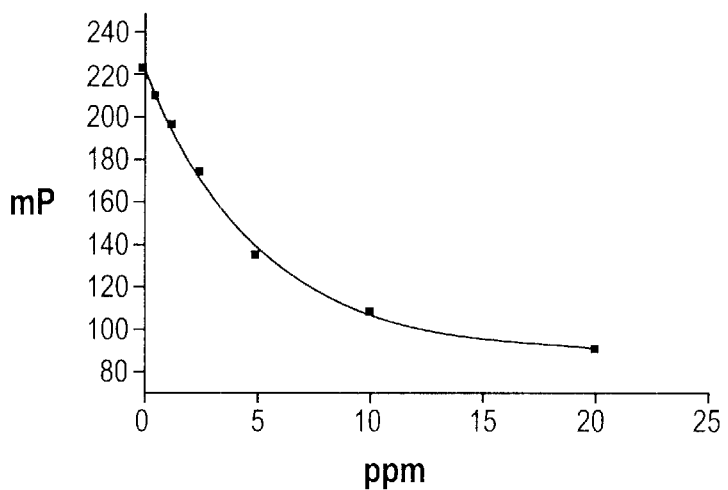
FIG. 1 is a standard curve for a fluorescence polarization assay for fumonisin in grains, using the data of Table 1, in accordance with a preferred embodiment of the present invention.

The preferred embodiments of the present invention provide a relatively simple homogeneous assay for fumonisin determination in grains that is based on measurements of fluorescence polarization. The technique of fluorescence polarization has been successfully utilized in various assay involving proteins, enzymes, drugs, DNA, hormones, peptides and antibodies.[12-16]

The principle behind the fluorescence polarization technique is as follows. Fluorescent probes having low molecular weight have low polarization values due to their fast rotation, whereas fluorescent probes with higher molecular weight have higher polarization due to their slower rotation. Thus the polarization value of a fluorophore increases upon binding to a target molecule. Further information about the fluorescence polarization technique is provided in U.S. Pat. Nos. 5,427,960 and 5,976,820 and in Nasir, M. S. and Jolley, M. E., "Fluorescence Polarization: An analytical tool for Immunoassay and Drug Discovery," *Combinatorial Chemistry & High Throughput Screening,* 1999, 2, 177–190, which references are incorporated herein by reference.

In the present invention, free fumonisin in the grain extract competes with fluorophore-conjugated fumonisin in the presence of an antibody giving rise to a change in polarization values depending upon the fumonisin concentration. Moreover, in accordance with preferred embodiments, fumonisin extraction is achieved using water that is substantially free of organic solvents, and the extraction is typically complete in 5 minutes. The subsequent steps may typically be accomplished quite rapidly, i.e., in about one minute. Accordingly, the preferred embodiments of the present invention provide a rapid, simple and quantitative method for the fumonisin analysis in various grains that requires only minimal training.

1. Materials and Methods

All the solvents and chemicals were used as received unless otherwise noted. Fluorescent compounds were purchased either from Sigma or Molecular probes. All other compounds were purchased from Sigma.

Grain samples containing variable amounts of fumonisin were obtained from the United States Department of Agriculture (USDA) in Peoria, Ill. Fumonisin standards were prepared either by dissolving a certain amount of solid fumonisin in buffer and diluting accordingly, or from a concentrated sample (1 mg/ml) obtained from the USDA. Fluorescence polarization measurements were carried out on a Sentry-FP model fluorescence polarization instrument (Diachemix Corp.).

A fumonisin monoclonal antibody designated below as "01 MAB" was obtained from Chris Maragos (USDA, Peoria, Ill.). Fumonisin antibodies designated "03 MAB" and "08 MAB" were obtained from Romer Labs, Union, Mo. The monoclonal antibodies were diluted as needed in PBSA, which is a phosphate buffer solution (pH about 7.4 to 7.5) containing 1 gram per liter sodium azide and 9 grams per liter sodium chloride.

For each fluorescence measurement, a 1 ml blank was prepared by adding 50 μL of sample to PBSA in a borosilicate tube (10×75 mm, VWR scientific) suitable for the Sentry-FP instrument. After taking a blank reading, 10 μl of suitably diluted tracer was added to the solution and a stable polarization value noted. A series of standards were run in this manner and a graph was plotted. Sample values were calculated accordingly.

2. Fumonisin Monoclonal Antibody Preparation

Fumonisin B1 was conjugated to a 1 mg/ml suspension of bovine serum albumin (BSA) at a fumonisin to protein ratio of 50:1 at 10° C. in 0.1 M phosphate buffer saline (PBS, pH~7.2). An equal volume of glutaraldehyde (2%, V/V) was added drop wise with constant stirring. After one hour, reaction was stopped by adding sodium borohydride to a final concentration of 10 mg/ml. After 1 hour the mixture was dialyzed for 72 hours with PBS. 1 mg (total protein) fractions were lyophilized and stored at −20° C. This lyophilized material was reconstituted with water before mice immunization. Further details are provided in Maragos, C. M., Bennett, G. A., Richard, J. L., *Food & Agricultural Immunology*, vol. 9, p. 3–12 (1997) and Azcona-Olivera, J. I., Abouzied, M. M., Plattner, R. D., Norred, W. P., Pestka, J. J., *Appl. & Environ. Microbiol.*, vol. 58, p. 169–173 (1992), which are incorporated herein by reference.

3. Preparation of $D_2$-Fumonisin Tracer

100 μL of a solution of fumonisin B1 (Sigma, 10 mg/ml in DMF) was mixed with 100 μL of 1M sodium carbonate solution. 100 μl of a solution of 6[{4,6-dichlorotriazin-2-yl}amino]fluorescein ("6-DTAF") hydrochloride (Sigma, 10 mg/ml in DMF) was then added, and, after thorough shaking, the reaction was incubated overnight at room temperature. A portion of the product mixture was separated by preparative TLC (silica, $CHCl_3:CH_3OH:CH_3CO_2H$, 30:5:0.5) and the product (Rf~0.3) was collected, shaken with methanol, centrifuged and filtered to give pure tracer. The remaining crude product was purified on a sephadex G-25 column using 0.01 M sodium phosphate (pH~7.5) solution as an eluant. The first 2 ml fraction was discarded and the second bright green fluorescent fraction was collected to give 5 ml of product. This stock solution was stored at 2–8° C. This fumonisin conjugate was diluted 1/200 for use. 10 μl of this diluted tracer in 1 ml PBS gave an intensity equivalent to ~1 nM fluorescein. This amount of the fumonisin conjugate was used for each test giving a tracer polarization of 40–50 mP. This tracer gave a mP of ~220 upon adding the appropriately diluted FB-1 antibody. One such batch provides approximately 10,000 tests.

4. Protocol for Fumonisin Fluorescence Polarization Assay

A preferred protocol for performing the fumonisin polarization assay is as follows. The grain sample being tested for fumonisin is crushed, and 20 grams of the crushed sample are added to 100 ml PBS (sodium phosphate buffer solution with a pH of about 7.4 to 7.5) in order to extract the fumonisin. The mixture should be shaken well. As described below, five minutes of vigorous shaking is typically adequate. A 1 ml aliquot of this mixture is taken and filtered with a fine filter. The filtered sample is then used for analysis.

In order to determine the amount of fumonisin present in the grain samples, a standard curve is first obtained using standard fumonisin B1 solutions as follows. A series of standards may be made by diluting appropriate amount of stock fumonisin B1 solution (1 mg/ml) into 1 ml PBSA buffer. 50 μl of standard is pipetted into 1 ml of diluted antibody solution in a 10×75 mm glass test tube, and the mixture is vortexed thoroughly. The diluted antibody solution is preferably 1/5000 in PBSA, with bovine gamma globulin (BGG) present at a concentration of 100 μg/ml. This mixture is used to perform a blank reading in the instrument. The readings should be repeated until they are stable (normally two readings). 10 μl of tracer is added to the glass test tube containing the antibody solution and standard, and the test tube is vortexed thoroughly. The test tube is placed back in the instrument, and mP values are recorded until they stabilize. The other standard solutions are read in the same way, and a standard curve is constructed using the stabilized mP values.

Once the calibration curve is obtained, the samples, prepared as described above, are measured in a similar manner. Specifically, 50 μl of sample is pipetted into 1 ml of diluted antibody solution in a 10×75 mm glass test tube. The mixture is vortexed thoroughly and used to perform a blank reading of the instrument. 10 μl of tracer is added to the glass test tube containing the antibody solution and sample, and the test tube is vortexed thoroughly. The test tube is placed back in the instrument, and mP values are recorded until they stabilize. The fumonisin concentration in the sample is then calculated using the standard curve.

It is recommended that the temperature of the laboratory be maintained constant during an experiment. Each time there is a change in temperature, the standard curve should be run again.

New pipette tips should be used with each pipetting activity to avoid contaminating the buffer preparation, each individual sample, or the tracer. The sample must not contain particulate chunks of matter visible to the eye. The pipette tip should be inserted just below the surface of the liquid when inserting sample. The lower portion of the glass test tube should not be handled because fingerprints can distort the FP value.

Buffer and diluted antibody solution should be stored at room temperature and must not be refrigerated. Temperature changes of more than a few degrees should be avoided. Tracer should be stored at 2 to 8 degrees Celsius when not in use. Instrument standards should also be stored at 2 to 8 degrees Celsius, but they should be allowed to warm to room temperature before use. Blank values should be within 300 intensity units before adding tracer. If unknown samples are run at a different time than the standard samples, a 0 and 1.25 ppm control reading should be performed before testing the unknowns in order to check the standard curve stability due to temperature variation.

5. Standard Curve For Fluorescence Polarization Assay of Fumonisin

A standard curve was obtained for the Sentry-FP fluorescence polarization instrument using the protocol described above for fumonisin B1 standards in various concentrations. Specifically, fumonisin B1 at concentrations of 0, 0.5, 1.25, 2.25, 5, 10, and 20 ppm were used. The fluorescence polarization readings in mP units for these fumonisin B1 standard solutions (in two separate runs) are listed in Table 1. FIG. 1 shows the standard curve, relating the fluorescence polarization signal in mP to fumonisin concentration in ppm, that was obtained from this data.

TABLE 1

| Fumonisin B1 standard concentration (ppm) | mP (first run) | mP (second run) |
|---|---|---|
| 0 | 224 | 223 |
| 0.5 | 211 | 210 |
| 1.25 | 195 | 197 |
| 2.5 | 173 | 175 |
| 5 | 136 | 135 |
| 10 | 108 | 108 |
| 20 | 90 | 91 |

6. Results of Fluorescence Polarization Assay For Fumonisin In Maize

A number of fumonisin contaminated maize samples (which were obtained from the USDA in Peoria, Ill.) was analyzed using the protocol described above. The samples in this study were designated 1, 2, 3, 4, 5, 6, 7, 12, 32, 33, 34, 35, 36, 37, 38, and 39. Each sample was divided into two or three fractions, designated as fractions A, B, and C below. 20 grams of each sample fraction were added to 100 ml PBS buffer, and the mixture shaken to extract the fumonisin, as described above. Portions of the extracts were filtered and analyzed in triplicate using the protocol described above. Some of the sample analysis portions were diluted in PBS buffer before they were analyzed. Table 2 lists the fluorescence polarization readings in mP units for each sample analysis portion, indicating whether the portion was diluted for analysis. Table 2 also lists the fumonisin concentration calculated for each sample analysis portion using the standard curve of FIG. 1. Sample analysis portions are designated in Table 2 by the sample number, the letter corresponding to the fraction used in a given extraction, and a number corresponding to the given extract portion that was analyzed. Thus, the sample analysis portion "5A1" refers to the first portion analyzed from the extract of the "A" fraction of sample "5." Table 3 lists the average calculated fumonisin concentrations (before dilution) for each sample fraction and the standard deviation.

TABLE 2

| Sample Analysis Portion | mP | Calculated Concentration (ppm) |
|---|---|---|
| 5A1 | 108 | 9.73 |
| (1 × 10 dilution) | | |
| 5A2 | 110 | 9.25 |
| (1 × 10 dilution) | | |
| 5A3 | 112 | 8.81 |
| (1 × 10 dilution) | | |
| 5B1 | 107 | 9.99 |
| (1 × 10 dilution) | | |
| 5B2 | 110 | 9.25 |
| (1 × 10 dilution) | | |
| 5B3 | 110 | 9.25 |
| (1 × 10 dilution) | | |
| 5C1 | 110 | 9.25 |
| (1 × 10 dilution) | | |
| 5C2 | 108 | 9.73 |
| (1 × 10 dilution) | | |
| 5C3 | 109 | 9.49 |
| (1 × 10 dilution) | | |
| 6A1 | 124 | 6.76 |
| 6A2 | 124 | 6.76 |
| 6A3 | 125 | 6.62 |
| 6B1 | 120 | 7.36 |
| 6B2 | 126 | 6.49 |
| 6B3 | 118 | 7.69 |
| 7A1 | 112 | 8.81 |
| 7A2 | 106 | 10.27 |
| 7A3 | 110 | 9.25 |
| 7B1 | 108 | 9.73 |
| 7B2 | 110 | 9.25 |
| 7B3 | 110 | 9.25 |
| 7C1 | 107 | 9.99 |
| 7C2 | 110 | 9.25 |
| 7C3 | 107 | 9.99 |
| 12A1 | 126 | 6.49 |
| 12A2 | 125 | 6.62 |
| 12A3 | 125 | 6.62 |
| 12B1 | 125 | 6.62 |
| 12B2 | 122 | 7.05 |
| 12B3 | 122 | 7.05 |
| 12C1 | 121 | 7.20 |
| 12C2 | 122 | 7.05 |
| 12C3 | 122 | 7.05 |
| 1A1 | 152 | 3.84 |
| (1 × 10 dilution) | | |
| 1A2 | 151 | 3.92 |
| (1 × 10 dilution) | | |
| 1A3 | 154 | 3.69 |
| (1 × 10 dilution) | | |
| 1B1 | 152 | 3.84 |
| (1 × 10 dilution) | | |
| 1B2 | 153 | 3.76 |
| (1 × 10 dilution) | | |
| 1B3 | 154 | 3.69 |
| (1 × 10 dilution) | | |
| 1C1 | 156 | 3.53 |
| (1 × 10 dilution) | | |
| 1C2 | 152 | 3.84 |
| (1 × 10 dilution) | | |
| 1C3 | 152 | 3.84 |
| (1 × 10 dilution) | | |
| 2A1 | 125 | 6.62 |
| (1 × 10 dilution) | | |
| 2A2 | 125 | 6.62 |
| (1 × 10 dilution) | | |
| 2A3 | 126 | 6.49 |
| (1 × 10 dilution) | | |
| 2B1 | 126 | 6.49 |
| (1 × 10 dilution) | | |
| 2B2 | 127 | 6.36 |
| (1 × 10 dilution) | | |
| 2B3 | 126 | 6.49 |
| (1 × 10 dilution) | | |
| 2C1 | 114 | 8.41 |
| (1 × 10 dilution) | | |
| 2C2 | 118 | 7.69 |
| (1 × 10 dilution) | | |
| 2C3 | 117 | 7.86 |
| (1 × 10 dilution) | | |
| 3A1 | 155 | 3.61 |
| (1 × 10 dilution) | | |
| 3A2 | 157 | 3.46 |
| (1 × 10 dilution) | | |
| 3A3 | 157 | 3.46 |
| (1 × 10 dilution) | | |
| 3B1 | 159 | 3.32 |
| (1 × 10 dilution) | | |
| 3B2 | 160 | 3.24 |
| (1 × 10 dilution) | | |
| 3B3 | 160 | 3.24 |

TABLE 2-continued

| Sample Analysis Portion | mP | Calculated Concentration (ppm) |
|---|---|---|
| 3C1 (1 × 10 dilution) | 158 | 3.39 |
| 3C2 (1 × 10 dilution) | 158 | 3.39 |
| 3C3 (1 × 10 dilution) | 160 | 3.24 |
| 4A1 (1 × 10 dilution) | 172 | 2.46 |
| 4A2 (1 × 10 dilution) | 171 | 2.52 |
| 4A3 (1 × 10 dilution) | 174 | 2.34 |
| 4B1 (1 × 10 dilution) | 170 | 2.58 |
| 4B2 (1 × 10 dilution) | 173 | 2.40 |
| 4B3 (1 × 10 dilution) | 172 | 2.46 |
| 4C1 (1 × 10 dilution) | 172 | 2.46 |
| 4C2 (1 × 10 dilution) | 173 | 2.40 |
| 4C3 (1 × 10 dilution) | 171 | 2.52 |
| 39A1 | 165 | 2.90 |
| 39A2 | 163 | 3.04 |
| 39A3 | 165 | 2.90 |
| 39B1 | 169 | 2.65 |
| 39B2 | 169 | 2.65 |
| 39B3 | 168 | 2.71 |
| 39C1 | 176 | 2.22 |
| 39C2 | 176 | 2.22 |
| 39C3 | 176 | 2.22 |
| 38A1 | 163 | 3.04 |
| 38A2 | 159 | 3.32 |
| 38A3 | 162 | 3.10 |
| 38B1 | 164 | 2.97 |
| 38B2 | 164 | 2.97 |
| 38B3 | 165 | 2.90 |
| 38C1 | 174 | 2.34 |
| 38C2 | 174 | 2.34 |
| 38C3 | 171 | 2.52 |
| 37A1 | 180 | 2.00 |
| 37A2 | 181 | 1.94 |
| 37A3 | 179 | 2.05 |
| 37B1 | 187 | 1.62 |
| 37B2 | 190 | 1.47 |
| 37B3 | 190 | 1.47 |
| 37C1 | 172 | 2.46 |
| 37C2 | 172 | 2.46 |
| 37C3 | 172 | 2.46 |
| 36A1 | 179 | 2.05 |
| 36A2 | 178 | 2.11 |
| 36A3 | 179 | 2.05 |
| 36B1 | 180 | 2.00 |
| 36B2 | 182 | 1.89 |
| 36B3 | 179 | 2.05 |
| 36C1 | 174 | 2.34 |
| 36C2 | 175 | 2.28 |
| 36C3 | 175 | 2.28 |
| 35A1 | 133 | 5.63 |
| 35A2 | 133 | 5.63 |
| 35A3 | 132 | 5.75 |
| 35B1 | 140 | 4.90 |
| 35B2 | 140 | 4.90 |
| 35B3 | 141 | 4.80 |
| 35C1 | 134 | 5.52 |
| 35C2 | 132 | 5.75 |
| 35C3 | 135 | 5.41 |
| 34A1 | 168 | 2.71 |
| 34A2 | 174 | 2.34 |
| 34A3 | 170 | 2.58 |
| 34B1 | 175 | 2.28 |
| 34B2 | 175 | 2.28 |
| 34B3 | 176 | 2.22 |
| 34C1 | 175 | 2.28 |
| 34C2 | 176 | 2.22 |
| 34C3 | 175 | 2.28 |
| 33A1 | 216 | 0.32 |
| 33A2 | 217 | 0.28 |
| 33A3 | 217 | 0.28 |
| 33B1 | 215 | 0.36 |
| 33B2 | 216 | 0.32 |
| 33B3 | 218 | 0.24 |
| 33C1 | 219 | 0.20 |
| 33C2 | 218 | 0.24 |
| 33C3 | 219 | 0.20 |
| 32A1 | 128 | 6.23 |
| 32A2 | 127 | 6.36 |
| 32B1 | 143 | 4.61 |
| 32B2 | 138 | 5.10 |
| 32C1 | 135 | 5.41 |
| 32C2 | 135 | 5.41 |

TABLE 3

| Sample | Average Calculated Fumonisin Concentration (ppm) | Standard Deviation |
|---|---|---|
| 5A | 92.68 | 4.60 |
| 5B | 95.00 | 4.27 |
| 5C | 94.92 | 2.41 |
| 6A | 6.72 | 0.08 |
| 6B | 7.18 | 0.62 |
| 7A | 9.44 | 0.74 |
| 7B | 9.41 | 0.28 |
| 7C | 9.75 | 0.43 |
| 12A | 6.58 | 0.08 |
| 12B | 6.91 | 0.25 |
| 12C | 7.10 | 0.09 |
| 1A | 38.18 | 1.20 |
| 1B | 37.65 | 0.78 |
| 1C | 37.40 | 1.78 |
| 2A | 65.79 | 0.78 |
| 2B | 64.45 | 0.76 |
| 2C | 79.85 | 3.78 |
| 3A | 35.10 | 0.86 |
| 3B | 32.68 | 0.41 |
| 3C | 33.40 | 0.83 |
| 4A | 24.41 | 0.92 |
| 4B | 24.81 | 0.93 |
| 4C | 24.61 | 0.61 |
| 39A | 2.95 | 0.08 |
| 39B | 2.67 | 0.04 |
| 39C | 2.22 | 0.00 |
| 38A | 3.15 | 0.15 |
| 38B | 2.95 | 0.04 |
| 38C | 2.40 | 0.10 |
| 37A | 2.00 | 0.06 |
| 37B | 1.52 | 0.09 |
| 37C | 2.46 | 0.00 |
| 36A | 2.07 | 0.03 |
| 36B | 1.98 | 0.08 |
| 36C | 2.30 | 0.03 |
| 35A | 5.67 | 0.07 |
| 35B | 4.87 | 0.06 |
| 35C | 5.56 | 0.17 |
| 34A | 2.54 | 0.19 |
| 34B | 2.26 | 0.03 |
| 34C | 2.26 | 0.03 |
| 33A | 0.29 | 0.02 |
| 33B | 0.30 | 0.06 |
| 33C | 0.21 | 0.02 |

TABLE 3-continued

| Sample | Average Calculated Fumonisin Concentration (ppm) | Standard Deviation |
|---|---|---|
| 32A | 5.73 | 0.97 |
| 32B | 5.04 | 0.40 |
| 32C | 5.41 | 0.00 |

Figure 2:
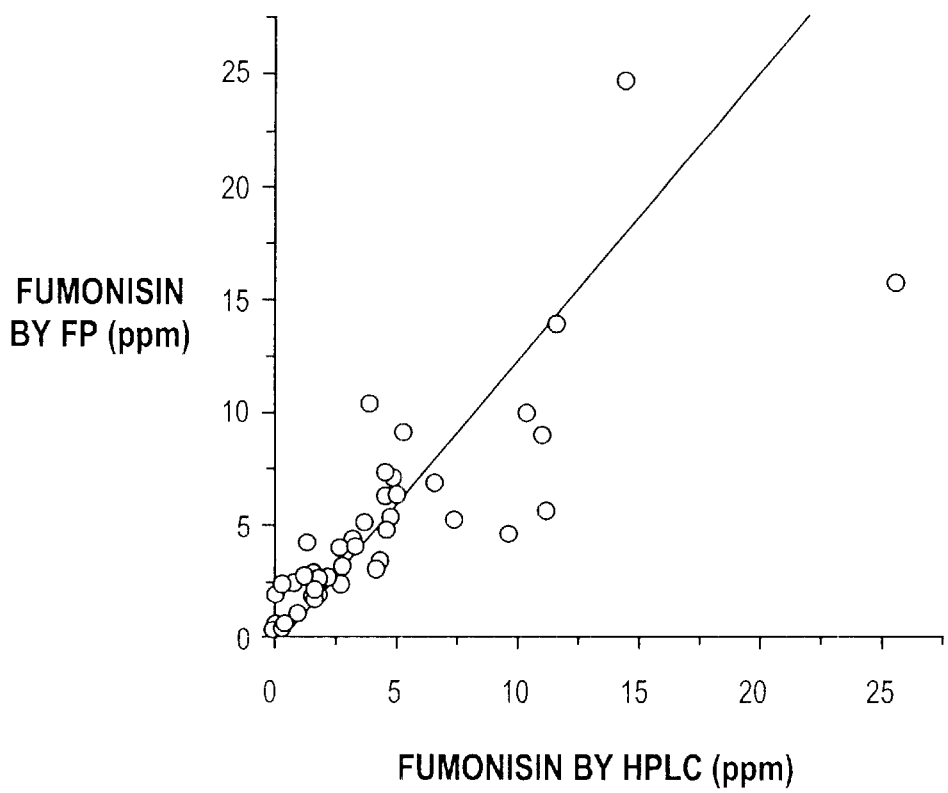
FIG. 2 is a graph comparing the calculated fumonisin concentrations for various samples obtained using an HPLC assay and the fluorescence polarization assay in accordance with a preferred embodiment of the present invention.

As an additional check on the accuracy of the fluorescence polarization assay, the fumonisin contaminated maize samples were also analyzed using HPLC. FIG. 2 is a graph comparing the fumonisin concentrations in the samples as measured using the fluorescence polarization and HPLC techniques. FIG. 2 shows good agreement between the two measurement techniques. The $r^2$ value for the data shown in FIG. 2 is 0.89, which indicates the fumonisin concentrations calculated using the two techniques are highly correlated.

7. Water Extraction of Fumonisin

Fumonisin has been historically extracted from corn using mixtures of $CH_3OH:H_2O$ (3:1) or $CH_3CN:H_2O$ (1:1).[2-3] All of these methods require relatively long and extensive shaking or stirring time and there is a debate about which solvent system is better for fumonisin extraction.[3-4] In view of the organic solvents used during extraction, various colored products are also extracted along with fumonisins and therefore require cleanup by various methods as solid phase extraction cartridges, strong anion exchange,[3] $C_{18}$ columns,[5] liquid-liquid partition,[6] or immunoaffinity chromatography.[7] With the availability of better grinders and shakers, it is preferable to use water or water solutions substantially free of organic solvents, for extraction of fumonisin. This minimizes the problem of extracting side colored products during fumonisin extraction in grains.

Figure 3:
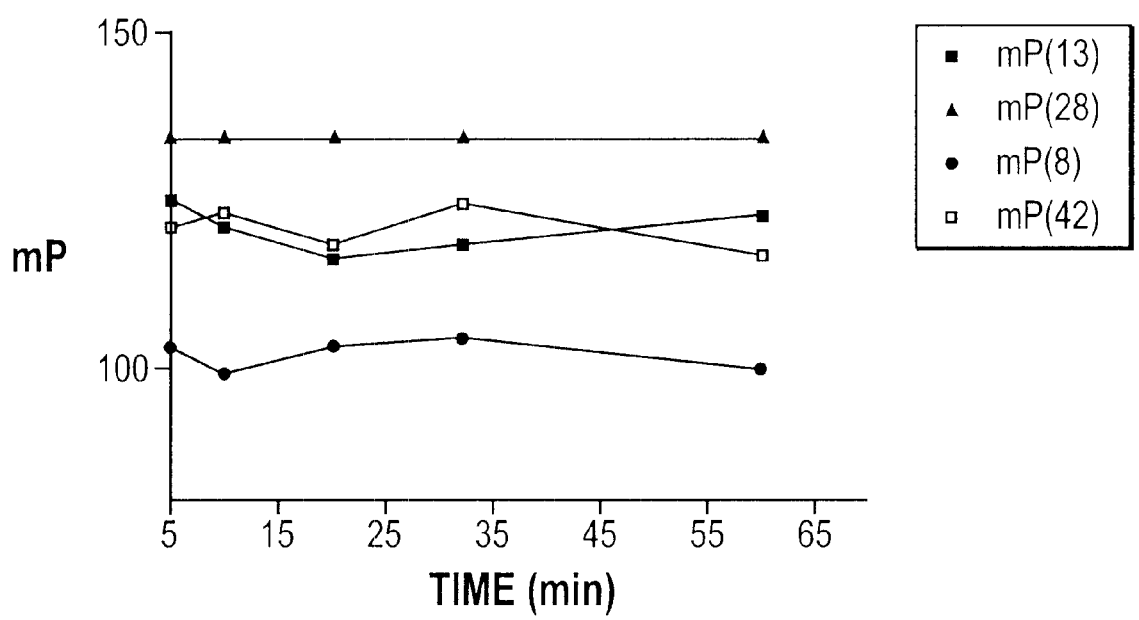
FIG. 3 is a graph showing the measured fluorescence polarization as a function of time for fumonisin extracted from grains, in accordance with a preferred embodiment of the present invention.

In order to find out the adequate time for water extraction, randomly chosen maize samples, designated 13, 28, 8, and 42 were studied. 20 grams of each of these samples were mixed with 100 ml PBS buffer and shaken over various lengths of time, namely, 5, 10, 20, 32, and 60 minutes. More particularly, in this study, the maize samples in buffer were shaken constantly for five minutes and then shaken periodically, about once every minute, after that. After each of these time periods, 50 µl of extract was taken out and added to 1 ml of diluted antibody solution (1/5000 into PBSA-BGG). The fluorescence polarization instrument was blanked using this mixture. 10 µl of tracer was then added and the fluorescence polarization was measured. The results are tabulated in Table 4 and plotted in FIG. 3. The results indicate that the extraction to be essentially complete in 5 minutes.

TABLE 4

| Time (minutes) | Sample 13 (mP) | Sample 28 (mP) | Sample 8 (mP) | Sample 42 (mP) |
|---|---|---|---|---|
| 5 | 125 | 134 | 103 | 121 |
| 10 | 121 | 134 | 99 | 123 |
| 20 | 116 | 134 | 103 | 118 |
| 32 | 118 | 134 | 104 | 124 |
| 60 | 122 | 135 | 99 | 116 |

8. Study of Fumonisin Assay for the Best Combination of Tracer-Antibody Binding A thorough study of all the available fumonisin tracers and antibodies was performed to find the best tracer and antibody for fumonisin determination. The following tracers were studied for this purpose: $D_2$-Fumonisin tracer, prepared by the reaction of fumonisin B1 with 6-DTAF, as described above; $D_1$-Fumonisin tracer, prepared by the reaction of fumonisin B1 with 5-DTAF (5[{4,6-dichlorotriazin-2-yl}amino]fluorescein); $F_2$-Fumonisin tracer, prepared by the reaction of fumonisin B1 with 6-carboxyfluorescein succinimidyl ester; $F_1$-Fumonisin tracer, prepared by the reaction of fumonisin B1 with 5-carboxyfluorescein succinimidyl ester; $I_2$-Fumonisin tracer, prepared by the reaction of fumonisin B1 with 6-Iodoacetamido fluorescein; 5FITC-Fumonisin tracer, prepared by the reaction of fumonisin B1 with 5-FITC (5[isothiocyanato]fluorescein); and 6FITC-Fumonisin tracer, prepared by the reaction of fumonisin B1 with 6-FITC (6[isothiocyanato]fluorescein). The monoclonal antibodies that were used were the "01 MAB" obtained from the USDA and the "03 MAB" and "08 MAB" obtained from Romer Labs.

The first experiment was run under conditions where the mixture was saturated with antibody. First, the fluorescence polarization of tracer in buffer without antibody was measured to obtain a tracer reading. Then, to reach saturated conditions, 1 ml of PBS was placed in a test tube with 2 µl of diluted antibody solution to get a blank reading. Tracer was then added until a stable mP value was obtained. The stable mp values for the various tracers and monoclonal antibodies in the study are listed in Table 5 below. The results in Table 5 indicate that, among the various tracers, $D_2$-Fumonisin and $F_2$-Fumonisin are the most sensitive, in that they had the highest stable mP values. No change from the tracer reading was observed when $I_2$-Fumonisin, 5FITC-Fumonisin, or 6FITC-Fumonisin tracer was added, indicating that these tracers had little or no sensitivity for these particular antibodies. As between the three different antibodies that were studies, the "01" and "08" antibodies had the highest stable mP value and, thus, the highest sensitivity.

TABLE 5

| Tracer | Antibody | Stable mP value |
|---|---|---|
| $D_2$-Fumonisin | 01 MAB | 241 |
| $D_2$-Fumonisin | 03 MAB | 121 |
| $D_2$-Fumonisin | 08 MAB | 194 |
| $D_1$-Fumonisin | 01 MAB | 160 |
| $D_1$-Fumonisin | 03 MAB | 130 |
| $D_1$-Fumonisin | 08 MAB | 150 |
| $I_2$-Fumonisin | 01 MAB | (no change) |
| $I_2$-Fumonisin | 03 MAB | (no change) |
| $I_2$-Fumonisin | 08 MAB | (no change) |
| $F_2$-Fumonisin | 01 MAB | 213 |
| $F_2$-Fumonisin | 03 MAB | 160 |
| $F_2$-Fumonisin | 08 MAB | 193 |
| $F_1$-Fumonisin | 01 MAB | 168 |
| $F_1$-Fumonisin | 03 MAB | 146 |
| $F_1$-Fumonisin | 08 MAB | 155 |
| 5FITC-Fumonisin | 01 MAB | (no change) |
| 5FITC-Fumonisin | 03 MAB | (no change) |
| 5FITC-Fumonisin | 08 MAB | (no change) |
| 6FITC-Fumonisin | 01 MAB | (no change) |
| 6FITC-Fumonisin | 03 MAB | (no change) |
| 6FITC-Fumonisin | 08 MAB | (no change) |

The next experiment was run in a regime in which only a limited quantity of antibody was present, in order for the assay to be sensitive towards free fumonisin. This experiment tested the two best tracers, $D_2$-Fumonisin and $F_2$-Fumonisin, and the two best antibodies, "01" and "08," from the previous experiment. Assays were performed by taking a blank with 1 ml buffer and adding enough of the antibody to achieve an antibody concentration of 1/10,000 for the $D_2$-Fumonisin studies and 1/5,000 for the $F_2$-Fumonisin studies. To this mixture was added 10 μl of tracer and a specified amount of 8 ppm fumonisin solution, and the stable fluorescence polarization value was recorded. The results are listed below in Table 6. These results indicate that the $D_2$-Fumonisin tracer and the "01" antibody together provide the highest sensitivity.

TABLE 6

| Tracer | Antibody | Amount of Fumonisin Added | Stable mP value |
| --- | --- | --- | --- |
| $D_2$-Fumonisin | 01 MAB | 0 μl | 162 |
| $D_2$-Fumonisin | 01 MAB | 10 μl | 85 |
| $D_2$-Fumonisin | 08 MAB | 0 μl | 123 |
| $D_2$-Fumonisin | 08 MAB | 10 μl | 91 |
| $F_2$-Fumonisin | 01 MAB | 0 μl | 166 |
| $F_2$-Fumonisin | 01 MAB | 10 μl | 86 |
| $F_2$-Fumonisin | 08 MAB | 0 μl | 160 |
| $F_2$-Fumonisin | 08 MAB | 10 μl | 110 |

9. Assay Kit

The materials used to perform the assay of the present invention are preferably made available in kit form. The kit preferably includes a quantity of extraction solution for extracting fumonisin from samples of grain, tracer and antibody in an amount suitable for at least one assay, along with suitable packaging and instructions for use. The tracer and antibody may be provided in solution, as a liquid dispersion, or as a substantially dry powder (e.g., in lyophilized form).

The suitable packaging can be any solid matrix or material, such as glass, plastic, paper, foil, and the like, capable of separately holding within fixed limits the buffer, tracer, and antibody. For example, the extraction solvent, tracer, and monoclonal antibody may be provided as solutions in separate labeled bottles or vials made of glass or plastic.

The antibody is specific for fumonisin and is preferably a monoclonal antibody. The preferred monoclonal antibody may be prepared as described herein and as known in the art.

The tracer comprises a fluorophore conjugated to a fumonisin, preferably fumonisin B1. Suitable fluorophores include 6-DTAF, 5-DTAF, 6-carboxyfluorescein, and 5-carboxyfluorescein. Other fluorophores may be used, provided the resulting tracer is able to bind with the monoclonal antibodies to produce a detectable change in fluorescence polarization. Preferably the tracer is either $D_2$-Fumonisin or $F_2$-Fumonisin, described above. Most preferably, the tracer is $D_2$-Fumonisin.

The extraction solvent is preferably an aqueous solvent that is substantially free of organic solvents. Most preferably, the extraction solvent is pure water or a buffer solution such as PBS.

10. References

1: (a) Romer Labs, Inc., Union, Mo., "Mycotoxin Resource Guide." Vol. 2, 1997. (b) Scott, P. M. "Fumonisins" Int. *J. Food. Microbiol.* 1993, 18, 257–270.
2: (a) Shephard, G. S.; Sydenham, E. W.; Thiel, P. G.; Gelderblom, W. C. A. "Quantitative determination of fumonisins $B_1$ and $B_2$ by HPLC with fluorescence detection." *J. Liq. Chromatogr.* 1990, 13, 2077–2087. (b) Sydenham, E. W.; Gelderblom, W. C. A.; Thiel, P. G.; Marasas, W. F. O. "Evidence for the natural occurrence of fumonisin $B_1$, a mycotoxin produced by *Fusarium moniliforme*, in corn." *J. Agric. Food. Chem.* 1990, 38, 285–290. (C) Thiel, P. G.; Sydenham, E. W.; Shephard, G. S.; Vanschalkwyk, D. J. "Study of the reproducibility characteristics of a liquid chromatographic method for the determination of fumonisin B-1 and B-2 in corn." *J. AOAC Int.* 1993, 76, 361–366.
3: Bennett, G. A.; Richard, J. L. "Liquid chromatographic method for analysis of the Naphthalene Dicarboxaldehyde derivative of fumonisins." *J. AOAC Int.* 1994, 77, 501–506.
4: Sydenham, E. W.; Shephard, G. S.; Thiel, P. G. "Liquid chromatographic determination of fumonisins $B_1$, $B_2$ and $B_3$ in foods and feeds." *J. AOAC Int.* 1992, 75, 313–318.
5: Wilson, T. M.; Ross, P. F.; Rice, L. G.; Osweiler, G. D.; Nelson, H. A.; Owens, D. L.; Plattner, R. D.; Reggiardo, C.; Noon, T. H.; Pickrell, J. W. "Fumonisin B1 levels associated with an epizootic of equine leukoencephalomalacia." *J. Vet. Diagn. Invest.* 1990, 2, 213–216.
6: Bagneris, R. W.; Carter, L. Jr.; Guerrero, H. G.; Ware, J. M. "Rapid HPLC detection and survey of fumonisin B1 in corn and corn screenings using fluorescence detection." $106^{th}$ *AOAC Int. Ann. Mtg.,* Cincinnati. 1992, 235.
7: Hansen, T. J.; Zabe, N. A.; Skipper, P. L. "Immunoaffinity isolation of fumonisin B1 and application to analysis in corn." $106^{th}$ *AOAC Int. Ann. Mtg., Cincinnati.* 1992, 230.
8: Norred, W. P.; Voss, K. A. "Toxicity and role of fumonisins in animal diseases and human esophageal cancer." *J. Food Prot.* 1994, 57, 522–527.
9: Rottinghaus, G. E.; Coatney, C. E.; Minor, H. C. "A rapid sensitive thin layer chromatography procedure for the detection of fumonisin B1 and B2. "*J. Vet. Diagn. Invest.* 1992, 4, 326–329.
10: Fukuda, S.; Nagahara, A.; Kikuchi, M.; Kumagai, S. "Preparation and characterization of antifumonisin monoclonal antibodies." *Biosci. Biotechnol. Biochem.* 1994, 58, 765–767.
11: Usleber, E.; Straka, M.; Terplan, G. "Enzyme immunoassay for fumonisin B1 applied to corn based food." *J. Agric. Food Chem.* 1994, 42, 1392–1396.
12: (a) Lynch, B. A.; Loiacono, K. A.; Tiong, C. L.; Adams, A. E.; MacNeil, I. A. "A fluorescence polarization based Src-SH2 binding assay." *Anal. Biochem.* 1997, 247, 77–82. (b) Wei, A. P.; Herron, J. N. Anal. Chem. 1993, 65, 3372–3377. ( c) Kauvar, L. M.; Higgins, D. L.; Viller, H. O.; Sportsman, J. R.; Engquist-Goldstein, A.; Bukar, R.; Bauer, K. E.; Dilley, H.; Rocke, D. M. *Chem. Biol.* 1995, 2, 107–118.
13: (a) Jolley, M. E. "Fluorescence polarization immunoassay for the determination of therapeutic drug levels in human plasma." *J. Anal. Toxicol.* 1981, 5, 236–240. (b) Eremin, S. A.; Gallacher, G.; Lotey, H.; Smith, D. S.; Landon, *J. Clin. Chem.* 1987, 33, 4113–4122. (c) Jolley, M. E. "Fluorescence polarization assays for the detection of proteases and their inhibitors." *J. Biomol. Screen.* 1996, 1, 33–38.
14: Nielsen, K.; Gall, D.; Jolley, M.; Leishman, G.; Balsevicius, S.; Smith, P.; Nicoletti, P.; Thomas, F. *J. Immun. Methods,* 1996, 195, 161–168.
15: Nasir, M. S.; Jolley, M. E. "Fluorescence Polarization: An analytical tool for Immunoassay and Drug Discovery." *Combinatorial Chemistry & High Throughput Screening,* 1999, 2, 177–190.
16: Tencza, S. B.; Islam, K. R.; Kalia, V.; Nasir, M. S.; Jolley, M. E.; Montelaro, R. C. "Development of a Fluorescence polarization-Based Diagnostic Assay for Equine Infectious Anemia Virus." *J. Clin. Microbiol.* 2000, 38, 1854–1859.

What is claimed is:

1. A homogeneous assay for fumonisin in grains, said homogeneous assay comprising the steps of:
   extracting fumonisin from a grain sample to provide an extract;
   combining said extract with a tracer and an antibody to provide a mixture, said antibody being specific for fumonisin, said tracer comprising fumonisin conjugated to a fluorophore, said tracer being able to bind to said antibody to produce a detectable change in fluorescence polarization;
   measuring the fluorescence polarization of said mixture to obtain a measured fluorescence polarization; and
   comparing said measured fluorescence polarization with a characterized fluorescence polarization value, said characterized fluorescence polarization value corresponding to a known fumonisin concentration.

2. The assay of claim 1, wherein said step of extracting fumonisin from a grain sample to provide an extract comprises the steps of:
   crushing said grain sample to provide a crushed grain sample; and
   shaking said crushed grain sample with a solvent for a predetermined time.

3. The assay of claim 2, wherein said solvent is an aqueous solvent that is substantially free of organic solvents.

4. The assay of claim 3, wherein said solvent is selected from the group consisting of water and buffer.

5. The assay of claim 1, wherein said fluorophore is selected from the group 5 consisting of 6[{4,6-dichlorotriazin-2-yl}amino]fluorescein, 5[{4,6-dichlorotriazin-2-yl}amino]fluorescein, 6-carboxyfluorescein, and 5-carboxyfluorescein.

6. The assay of claim 5, wherein said fluorophore is selected from the group consisting of 6[{4,6-dichlorotriazin-2-yl}amino]fluorescein and 6-carboxyfluorescein.

7. The assay of claim 6, wherein said fluorophore is 6[{4,6-dichlorotriazin-2-yl}amino]fluorescein.

8. The assay of claim 1, further comprising the steps of:
   providing a plurality of fumonisin standard solutions, each of said fumonisin standard solutions having a different known concentration;
   adding said tracer and said antibody to each one of said plurality of fumonisin standard solutions, so as to provide a plurality of standard mixtures; and
   measuring the fluorescence polarization of each one of said plurality of said standard mixtures to provide a plurality of standard fluorescence polarization values corresponding to known fumonisin concentrations.

9. The assay of claim 8, wherein said characterized fluorescence polarization value is one of said standard fluorescence polarization values.

10. An assay kit for characterizing fumonisin content in grains, said assay kit comprising:
    an antibody, and a tracer, each in an amount suitable for at least one homogeneous fluorescence polarization assay for fumonisin in grains, packaging, and instructions for using said antibody and said tracer in said homogeneous fluorescence polarization assay, said antibody being specific for fumonisin, said tracer comprising fumonisin conjugated to a fluorophore, said tracer being able to bind to said antibody to produce a detectable change in fluorescence polarization.

11. The assay kit of claim 10, further comprising an extraction solvent for extracting fumonisin in grains.

12. The assay kit of claim 11, wherein said extraction solvent is an aqueous solvent that is substantially free of organic solvents.

13. The assay kit of claim 12, wherein said extraction solvent is selected from the group consisting of water and buffer.

14. The assay kit of claim 10, wherein said fluorophore is selected from the group consisting of 6[{4,6-dichlorotriazin-2-yl}amino]fluorescein, 5[{4,6-dichlorotriazin-2-yl}amino]fluorescein, 6-carboxyfluorescein, and 5-carboxyfluorescein.

15. The assay kit of claim 14, wherein said fluorophore is selected from the group consisting of 6[{4,6-dichlorotriazin-2-yl}amino]fluorescein and 6-carboxyfluorescein.

16. The assay kit of claim 15, wherein said fluorophore is 6[{4,6-dichlorotriazin-2-yl}amino]fluorescein.

* * * * *